(12) United States Patent
von Schuckmann

(10) Patent No.: US 8,915,246 B2
(45) Date of Patent: Dec. 23, 2014

(54) DOSING DEVICE

(75) Inventor: Alfred von Schuckmann, Kevelaer (DE)

(73) Assignee: Sanofi SA, Meyrin (CH)

( * ) Notice: Subject to any disclaimer, the term of this patent is extended or adjusted under 35 U.S.C. 154(b) by 626 days.

(21) Appl. No.: 13/141,649

(22) PCT Filed: Dec. 28, 2009

(86) PCT No.: PCT/EP2009/067948
§ 371 (c)(1),
(2), (4) Date: Oct. 4, 2011

(87) PCT Pub. No.: WO2010/076302
PCT Pub. Date: Jul. 8, 2010

(65) Prior Publication Data
US 2012/0017903 A1 Jan. 26, 2012

(30) Foreign Application Priority Data
Dec. 30, 2008 (DE) .................... 20 2008 017 185 U

(51) Int. Cl.
*A61M 16/00* (2006.01)
*A61M 15/00* (2006.01)
*B05D 7/14* (2006.01)
*B65D 83/06* (2006.01)

(52) U.S. Cl.
CPC ....... *A61M 15/0065* (2013.01); *A61M 15/0078* (2014.02); *A61M 2202/064* (2013.01)
USPC .................................................. 128/203.15

(58) Field of Classification Search
CPC .......... A61M 15/00; A61M 2015/003; A61M 15/0065; A61M 2015/0068; A61M 2015/007; A61M 2015/0071; A61M 2015/0078

USPC ............ 128/203.15, 203.19, 203.21, 205.23; 222/23, 36, 45, 47, 49, 154, 157
See application file for complete search history.

(56) References Cited

U.S. PATENT DOCUMENTS 5,230,714 A 7/1993 Steckel
5,320,714 A 6/1994 Brendel
(Continued)

FOREIGN PATENT DOCUMENTS

CN 1205769 6/2005
CN 1946448 4/2007
(Continued)

OTHER PUBLICATIONS

International Search Report for International App. No. PCT/EP2009/067948, mailed Apr. 1, 2010.

*Primary Examiner* — Kristen Matter
(74) *Attorney, Agent, or Firm* — McDonnell Boehnen Hulbert & Berghoff LLP

(57) ABSTRACT

The invention relates to a dosing device for inhaling a powdery substance, particularly of a medical nature, which is arranged in a storage chamber above a trailing bottom and can be brought from said storage chamber into an evacuation readiness position, and having a display (A) associated with the actual filling level in the area of the device wall. In order to further develop a dosing device of the type in question particularly with regard to an improved display in an advantageous manner, it is proposed that the display (A) be composed of a strip tape carried along by the bottom and deflected by 180°, wherein the deflection area of the strip tape lies behind the transparent device wall.

3 Claims, 6 Drawing Sheets

(56) References Cited

U.S. PATENT DOCUMENTS

| | | | |
|---|---|---|---|
| 6,071,498 A | 6/2000 | Narodylo et al. | |
| 6,149,054 A | 11/2000 | Cirrillo et al. | |
| 6,701,917 B2 | 3/2004 | O'Leary | |
| 6,752,147 B1 | 6/2004 | Goldemann et al. | |
| 2002/0073996 A1* | 6/2002 | O'Leary | 128/203.15 |
| 2006/0118106 A1 | 6/2006 | Von Schuckmann | |
| 2008/0223365 A1 | 9/2008 | Von Schuckmann | |

FOREIGN PATENT DOCUMENTS

| | | |
|---|---|---|
| CN | 101048187 | 10/2007 |
| DE | 19522415 | 1/1997 |
| DE | 19524033 | 1/1997 |
| DE | 19825434 | 8/1999 |
| EP | 1905472 | 4/2008 |
| EP | 1905473 | 4/2008 |
| RU | 2323749 | 5/2008 |
| WO | 2005/102430 | 11/2005 |

* cited by examiner

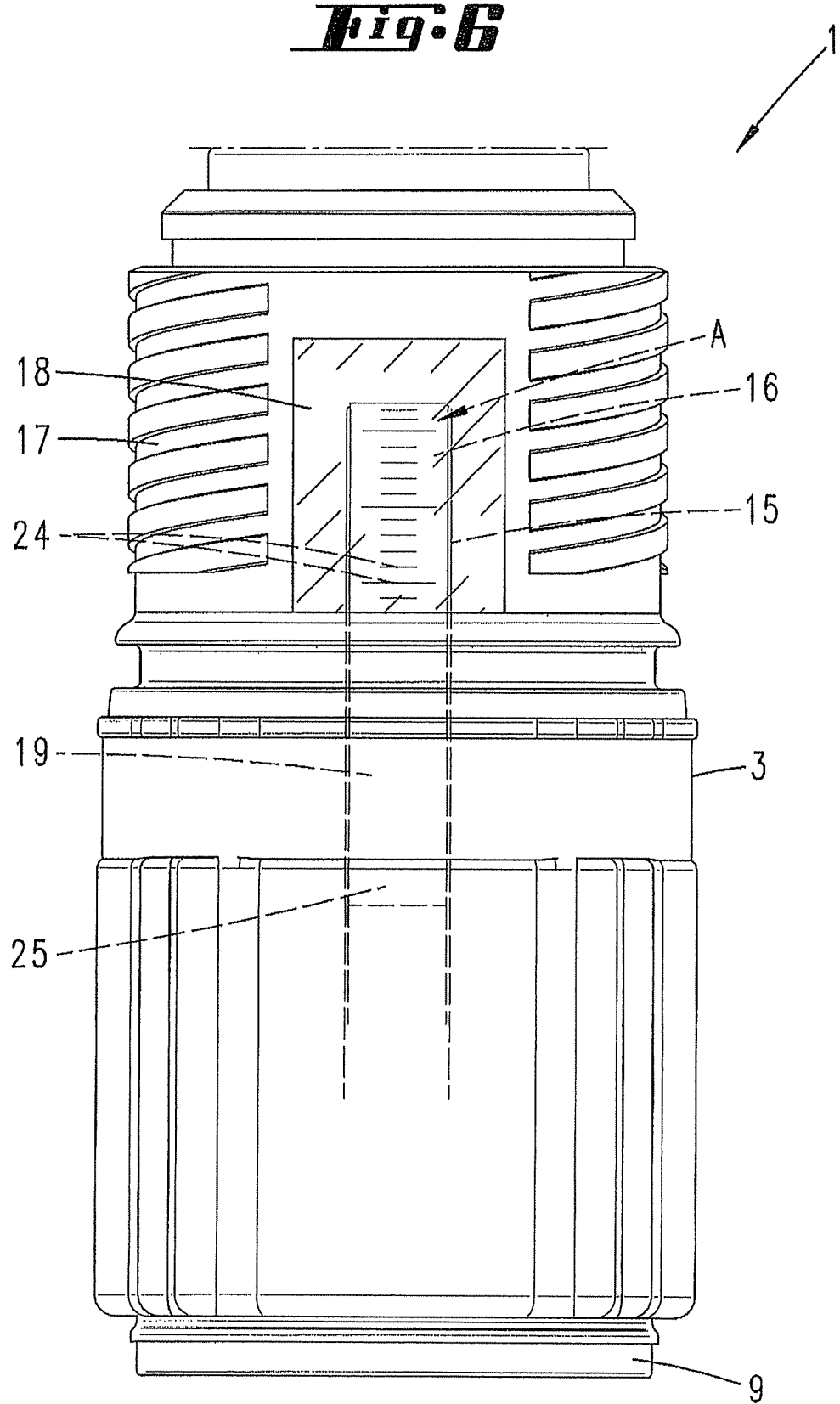

DOSING DEVICE

CROSS REFERENCE TO RELATED APPLICATIONS

The present application is a U.S. National Phase Application pursuant to 35 U.S.C. §371 of International Application No. PCT/EP2009/067948 filed Dec. 28, 2009, which claims priority to German Patent Application No. 202008017185.7 filed on Dec. 30, 2008. The entire disclosure contents of these applications are herewith incorporated by reference into the present application.

FIELD OF THE INVENTION

The invention relates to a dosing device for inhaling a powdery substance, particularly of a medical nature, which is arranged in a storage chamber above a trailing bottom and can be brought from said storage chamber into an emptying readiness position, and having a display associated with the actual filling level in the area of the device wall.

BACKGROUND

Dosing devices of the type under discussion are known. These are used for the dosed inhalation of a predetermined partial quantity of the powdery substance accommodated in the storage chamber, further for oral and/or nasal inhalation. In preparation, if appropriate in the course of the inhalation, a predetermined partial quantity is removed from the storage chamber for this purpose and brought into an emptying readiness position, from which the quantity divided off is transferred into the suction air stream in the course of the inhalation. Corresponding to the quantity of powder removed, the bottom of the storage chamber trails after the powder removal, possibly with spring assistance. Accordingly, depending on the inhalation operations, the bottom moves gradually in the direction of the storage chamber ceiling, reducing the chamber filling volume. In order to provide the user with information about the number of inhalation operations already carried out or about the number still remaining, it is further known to provide a display assigned to the actual filling level.

SUMMARY

In view of the known prior art, a technical problem of the invention is seen in developing a dosing device of the type under discussion further in an advantageous way, in particular with regard to an improved display. This problem is firstly and substantially solved by the subject matter of the claims, wherein it is proposed that the display be composed of a strip tape carried along by the bottom and deflected by 180°, wherein the deflection area of the strip tape lies behind the transparent device wall. As a result of this configuration, an improved display is created, in particular a display that can be read in an improved way by the user. The quantity of powder removed from the storage chamber in order to prepare an inhalation operation is generally so low that a correspondingly low bottom trailing movement results from this. An immediate display, derived from the bottom movement, can barely be read or read only with difficulty as a result of the above-described problems. In this case, no noticeable difference of the display position with respect to the previous position before the inhalation operation carried out can be detected. By means of the arrangement of the strip tape carried along by the bottom and deflected by 180°, a mechanical advantage is achieved, so that, in the area of the display, with a simple 180° deflection, a doubling of the strip tape displacement travel with respect to the bottom displacement travel is carried out. The display displacement is accordingly more easily detectable by the user. The deflection area of the strip tape that is carried along is additionally the display region for the actual state that can be detected visually by the user through the transparent device wall. In a preferred refinement, a 180° deflection of the strip tape is provided for the corresponding 2:1 mechanical advantage of the bottom displacement travel. In a further refinement, two or more 180° deflections can also be provided, for the corresponding further increase in the mechanical advantage ratio and the increased sensitivity of the display resulting therefrom. Furthermore, the strip tape is provided with a marking facing the viewing window or the transparent device wall and/or a color variation, wherein the marking or the color in the area of the deflection corresponds to the display value, correspondingly further representing the number of inhalation operations still to be carried out or alternatively the number of inhalation operations already carried out.

Further features of the invention are explained below, also in the figures and description, often in the preferred association thereof with the subject matter of the claims or with features of further claims. However, they can also be important in association with just the individual features of the claims or the respective further claim or in each case independently.

Thus, in one preferred refinement, it is further provided for the deflection point to form a beveled surface on the inner side and for the deflection point facing the transparent device wall to be configured more edged by comparison. As a result of this refinement, a 180° deflection that is gentle overall is achieved. The stressing of the strip tape carried along over the deflection edge is reduced substantially as compared with a hard 180° deflection. To this end, in particular the deflection point of the deflection edge that faces away from the transparent device wall is beveled, so that, on this basis, instead of a hard 90° deflection, a subdivided deflection of preferably twice 45° can be achieved. For the unambiguous display of the actual state of the filling level of the storage chamber, the deflection point facing the transparent device wall is configured more angularly as compared with the deflection point facing inward, further providing a direct 90° deflection, for example, wherein it is further preferred, for the purpose of looking after the material of the strip tape, to form this deflection point to be rounded in cross section or to run with a bevel. Since the strip tape section assigned to the deflection point facing the transparent device wall represents the display value, in the exemplary case of appropriate rounding of the deflection point, a radius in the tenths of a millimeter range is chosen, so that the unambiguity of the display is correspondingly provided.

BRIEF DESCRIPTION OF THE FIGURES

In the following text, the invention is explained in more detail by using the appended drawing, which merely represents one exemplary embodiment and in which:

FIG. 6 shows an illustration corresponding to FIG. 4 but relating to the position according to FIG. 5.

DETAILED DESCRIPTION

Figure 1:
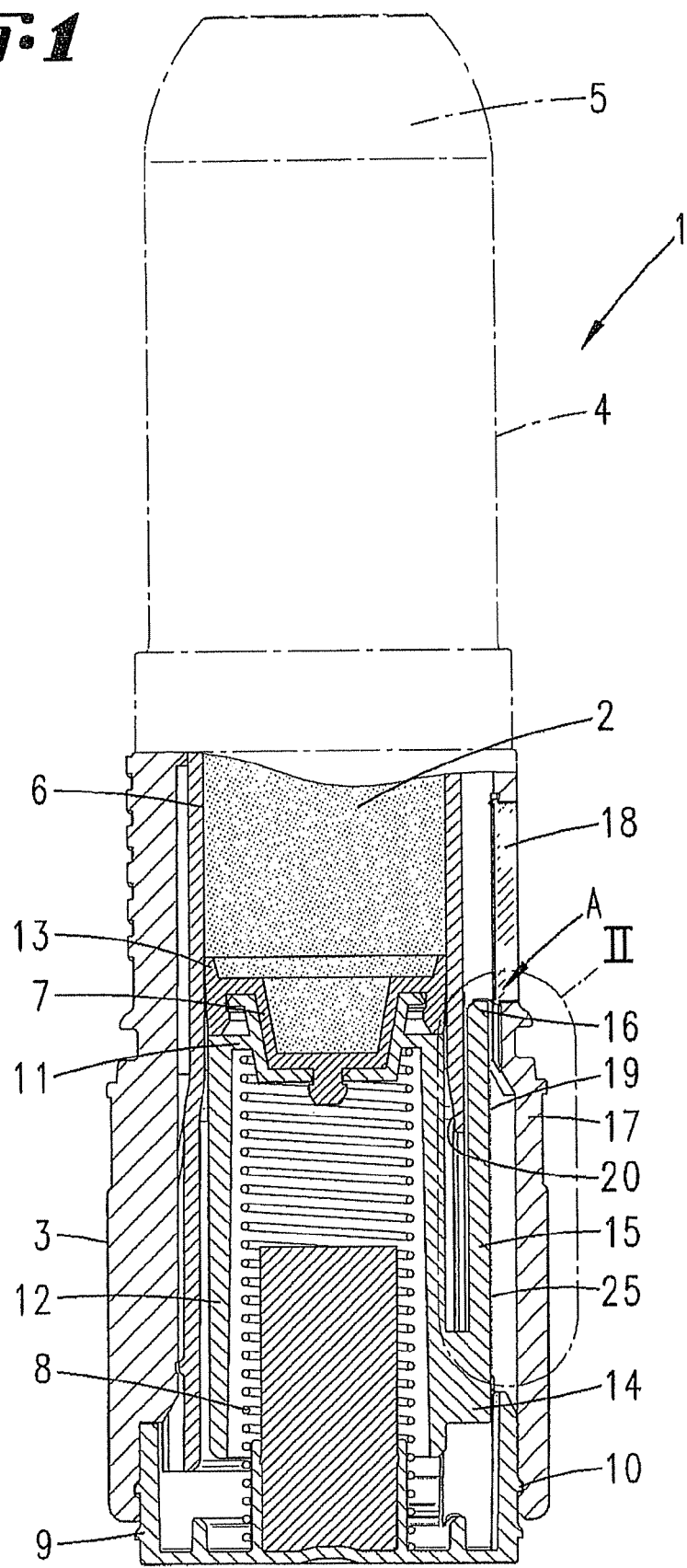
FIG. 1 shows the dosing device in a partially sectioned view, relating to the basic position of the dosing device before first use.
Figure 2:
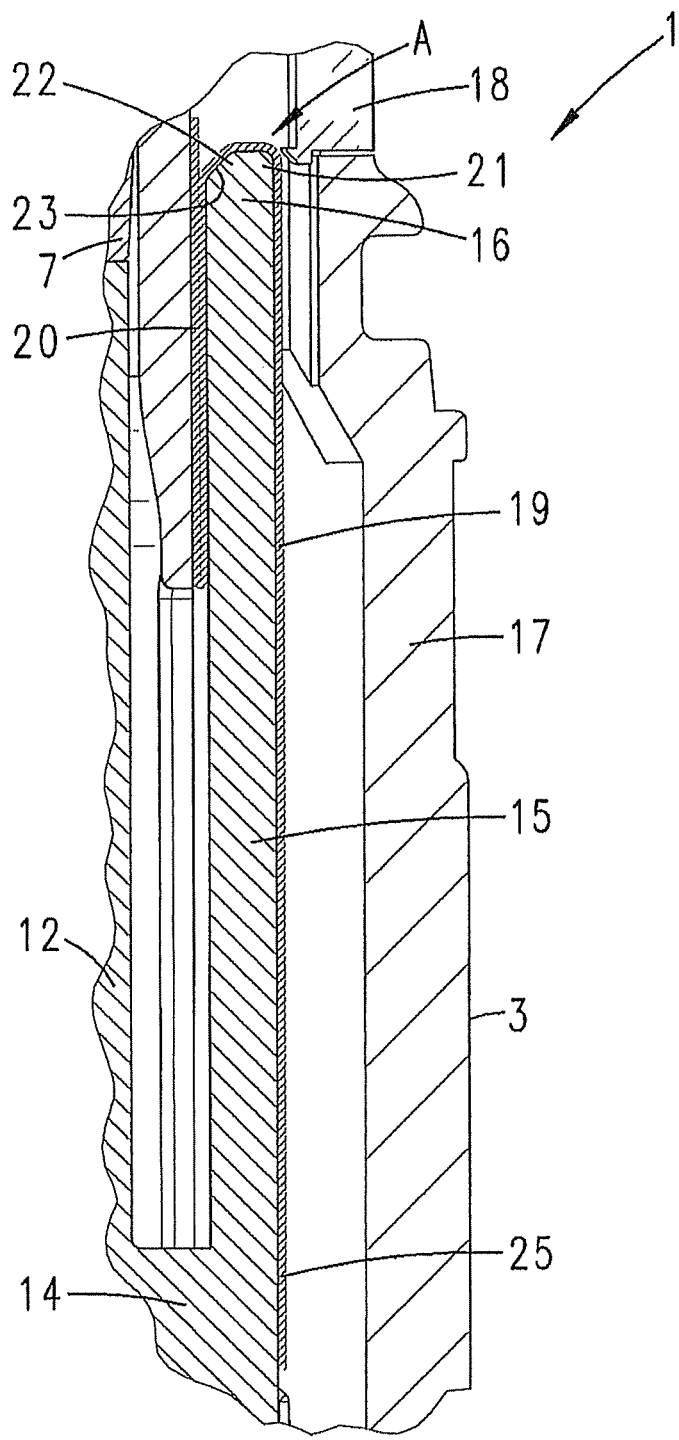
FIG. 2. shows the enlargement of the area II in FIG. 1.
Figure 3:
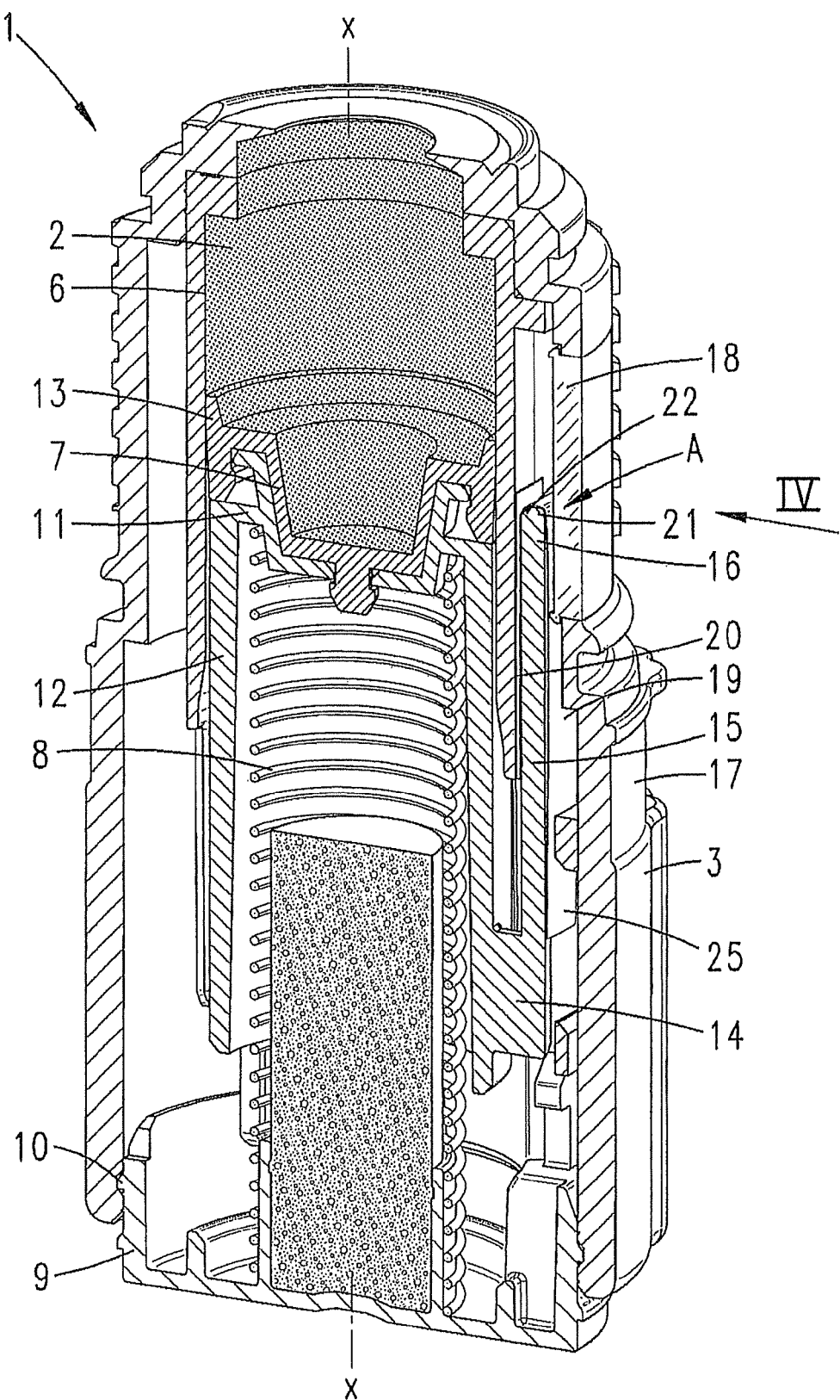
FIG. 3. shows a perspective sectional illustration of the area of the dosing device sectioned in FIG. 1, relating to an intermediate position.
Figure 4:
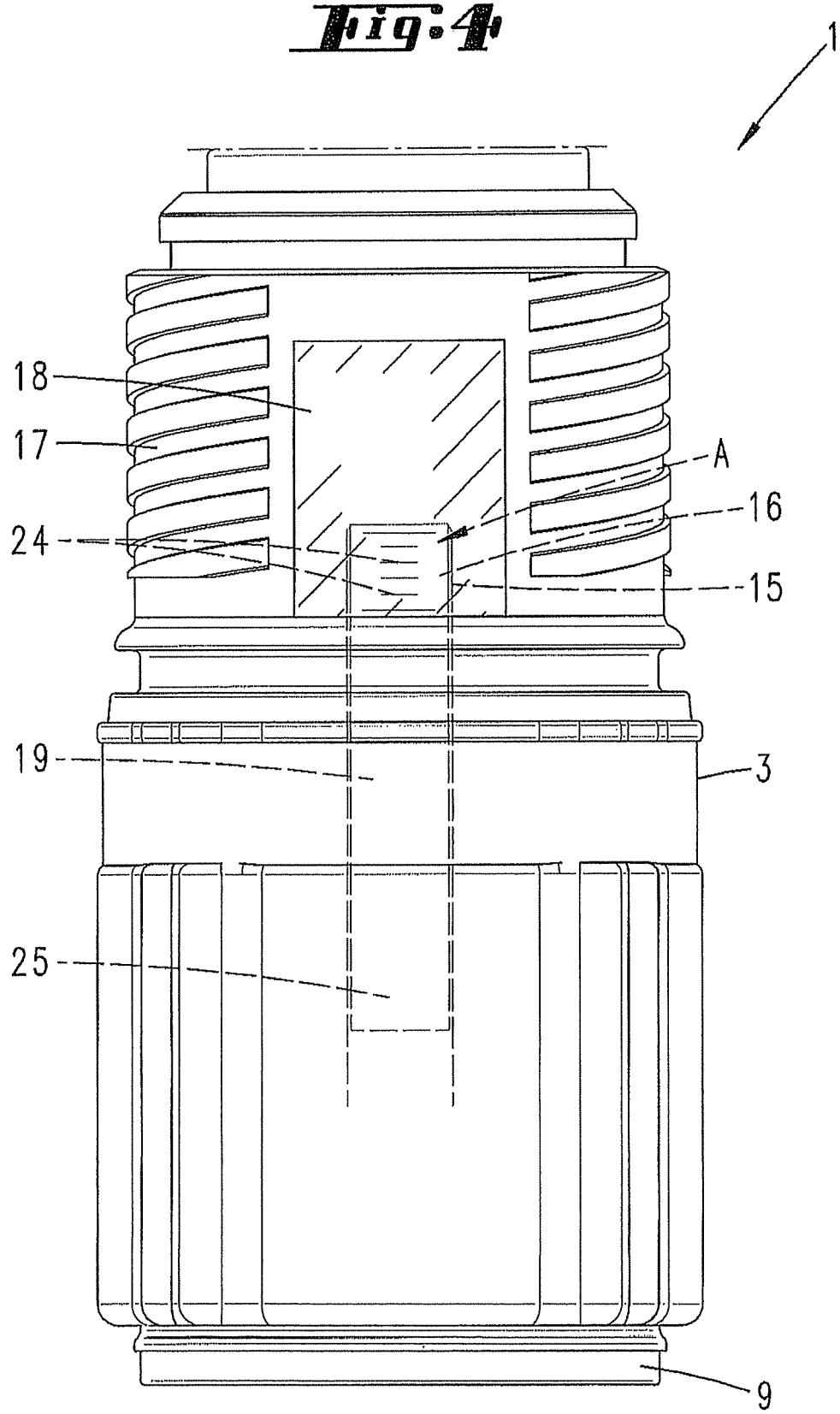
FIG. 4 shows the view toward the dosing device area according to the arrow IV in FIG. 3.
Figure 5:
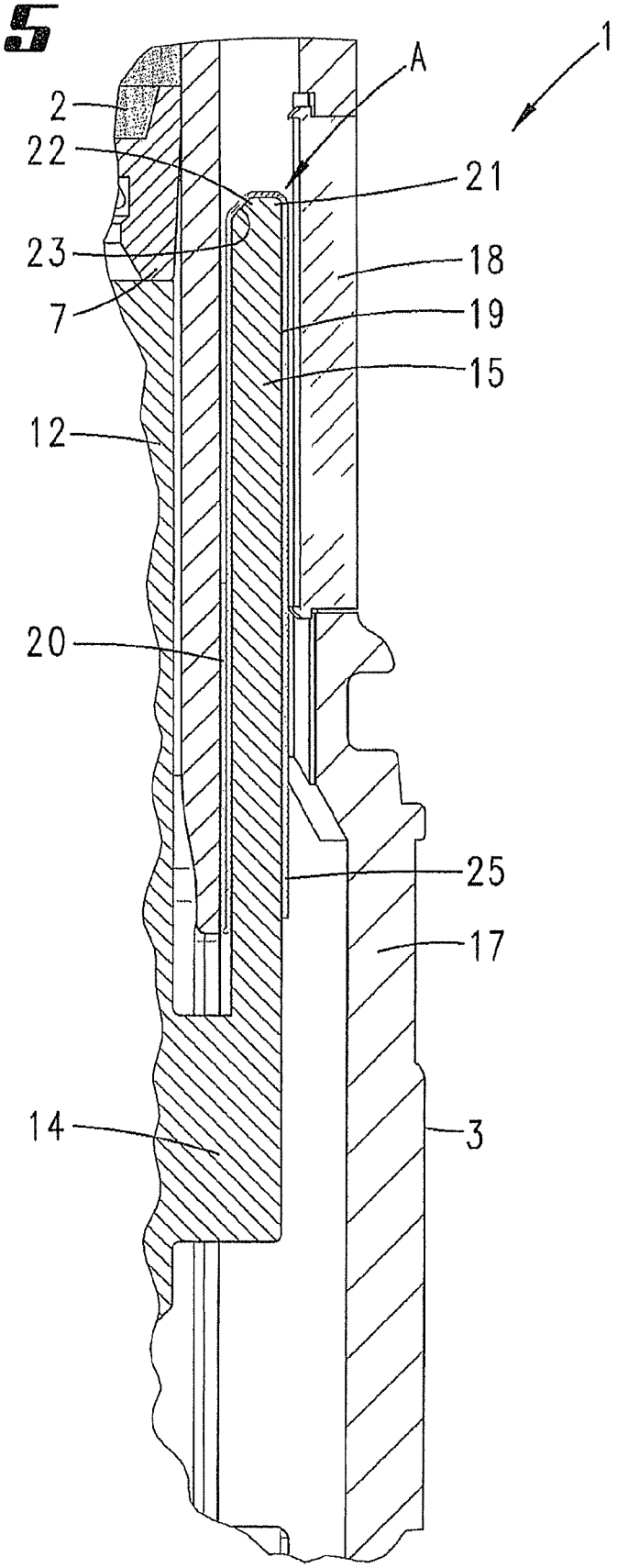
FIG. 5 shows a detailed sectional illustration corresponding to FIG. 2 but relating to a further intermediate position after carrying out a number of inhalation operations and corresponding substance removal from the storage chamber.

The dosing device 1 illustrated in the figures for inhaling a powdery substance 2, particularly of a medical nature, is implemented as a pocket device in the shape of a short rod that can be carried conveniently, having a cylindrical casing 3 that determines the shape.

The cylindrical tube-like casing 3 has at the top an outer cylinder, the free end of which forms a mouthpiece 5. The latter is formed to be suitable for the mouth, for example flattened. The mouthpiece 5 can be covered in a protective manner by means of a beaker-like closure cap, not illustrated.

The substance 2 is accommodated in a storage chamber 6 of the casing 3 (possibly refillable). Via a dosing device, not illustrated, in preparation for an inhalation operation a partial quantity of substance is conveyed to a transfer point located outside the storage chamber 6, the partial quantity accordingly being brought into an emptying readiness position.

The dosable substance is a (normally medical) powdery substance 2. It can be, for example, a basic body capable of transport in a suction stream, such as a lactose excipient, for micronized fine drug particles adhering to the surface.

The lower end of the storage chamber 6 is formed by a pot-like bottom 7, which is spring loaded in the direction of the mouthpiece 5 by means of a compression spring 8. The compression spring 8 is supported with the bottom end turn on a bottom cap 9 sealing off the casing 3 there. The latter, here, is in latching engagement with the section of the casing 3 with enlarged cross section on the inner side of the wall, wherein a corresponding latching collar 10 of the bottom cap 9 engages in a matching annular notch in the casing 3.

The end turn at the top of the pre-biased compression spring 8 acts in a loading manner on an inner shoulder 11 of a hollow piston 12 of the piston-like contrivance 7/12. As can be seen in particular from the illustration in FIG. 1, the stepped pot-like bottom 7 is connected in a latching manner to the hollow piston 12 in the area of the inner shoulder 11.

The rim of the pot of the bottom 7 provides an annular lip 13 which, on account of its rubbery-elastic material, wipes off the wall of the storage chamber 6 without loss.

The compression spring 8 in the exemplary embodiment illustrated is a cylindrical spring having a length, measured in the unstressed state, which corresponds approximately to ten times the maximum pressing length. The pressing length is defined by the extent of the axial displacement of the bottom 7 between a lower position according to FIG. 1, corresponding to the filling position, and an upper position of the bottom 17, limited by a stop, in the storage chamber 6. Thus, in the exemplary embodiment illustrated, such a pressing length of 15 mm is provided. As a result of the spring configuration, in particular as a result of the spring length chosen, a constant spring pressure on the bottom 7 is achieved over the entire pressing length, which leads to uniform compaction of the substance over the entire time period of use of the device 1.

The trailing bottom includes the hollow piston 12 and a radial outrigger 14 and is connected in a latching manner to the bottom 7. The radial outrigger 14 is integrally formed with a finger-like protrusion 15 aligned axially in the direction of the plane of the bottom 7 and reaching over the outside of the storage chamber wall. As a result of the attachment of the protrusion 15 to the hollow piston 12, the axial position of the protrusion 15, in particular the axial position of the free end 16 of the protrusion 15, depends directly on the axial position of the bottom 7.

In association with the free end 16 of the protrusion 15, the device wall 17 of the casing 3 is configured to be transparent, and accordingly forms a viewing window 18. The height of the viewing window 18, seen in the axial extent of the dosing device 1, is matched to the maximum extent of the axial displacement of the bottom 7 in the storage chamber 6 between the lower position of said bottom and the upper position limited by the stop. This upper position of the bottom 7, limited by the stop, corresponds to the empty position of the storage chamber 6, i.e. the position from which no further inhalation can be carried out, although it is entirely possible for a substance residue that can no longer be extracted to remain in the storage chamber 6.

The protrusion 15 interacts with a strip tape 19. The latter is attached to the storage chamber wall in the area of a free end in the overlap area of protrusion 15 and storage chamber wall, for example adhesively bonded or welded to the storage chamber wall in the case of a configuration of the strip tape 19 from plastic material.

Starting from this tape attachment 20, the strip tape 19 firstly extends along the surface of the protrusion 15 facing the storage chamber wall. Following a 180° deflection around the free end 16 of the protrusion 15, the strip tape 19 runs downward along the radially outwardly directed surface of the protrusion 15 in the direction of the bottom section of the dosing device 1. The strip tape 19 rests loosely on the respectively associated surfaces of the protrusion 15 for the sliding displacement of said tape.

As a result of this arrangement, a display A for the visual transmission of the filling level of the storage chamber 6 is achieved. The direct movement of the protrusion 15 resulting from the axial displacement of the bottom 7 is transmitted indirectly to the strip tape 19 fixed at one end to an area that is fixed to the casing and thus cannot move axially, and laid loosely through 180° around the protrusion 15. An axial movement of the protrusion 15 resulting from a displacement of the bottom 7 following a removal of part of the substance from the storage chamber 6 is transferred to the strip tape 19 in accordance with the block and tackle principle, so that a mechanical advantage ratio of 1:2 between the extent of the axial displacement of the protrusion and the extent of the axial displacement of the strip tape is achieved in the area of the section resting freely on the outside of the protrusion 15.

In the course of the gradual axial displacement of the protrusion 15 carried out gradually as a function of the removal of part of the substance from the storage chamber 6, the free end of the protrusion 15 moves upward visibly behind the viewing window 18, this with a corresponding carrying along of the strip tape 19 with a mechanical advantage, the deflection point 21 of the protrusion 15 facing the viewing window 18 defining the display value on the strip tape 19. In the exemplary embodiment illustrated, this deflection point 21 is shaped with a relatively sharp edge in cross section, only provided with a rounded portion, the radius of which lies in the tenths of a millimeter range. Thus, an angular deflection point 21 is formed, by which means the ability to read the display A unambiguously is achieved.

The deflection point 22 facing inwardly, i.e. facing away from the outer deflection point 21, is blunted as compared with the deflection point 21, this being done by forming a beveled surface 23. As a result of this configuration, in the exemplary embodiment illustrated, the strip tape 19 led over the free end 16 of the protrusion 15 is led on the inside over two 45° deflection areas following each other in the strip tape longitudinal extent. This proves to take care of the material for the strip tape 19. In an alternative refinement, the deflection point 22 can be rounded in cross section in the same way as the outer deflection point 21, this further preferred with a radius enlarged substantially as compared with the deflection point 21.

As shown in the figures, the strip tape 19 is provided with a scale 24 on the visible side, i.e. on the side facing the viewing window 18 in the area of the deflection point 21. This shows the number of inhalations that can still be carried out, indirectly the number of quantities of substance still to be divided off from the storage chamber 6. Alternatively, via the display A or via the scale 24, the number of inhalations already carried out can also be displayed.

Further alternatively, the strip tape 19 is provided on the visible side with a color variation. For instance, the loose free end 25 of the strip tape 19 which, shortly before the stopping of the bottom 7 in the uppermost position, gets into the viewing window area and further into the area of the deflection point 21, is provided with a warning color, for example red, while the remaining visible area of the strip tape 19 has a neutral color by contrast, such as yellow.

All the features disclosed are (per se) important to the invention. Also incorporated hereby in the disclosure of the application is the entire content of the disclosure of the associated/appended priority documents (copy of the prior application), including for the purpose of incorporating features of these documents in claims of the present application.

The invention claimed is:

1. A dosing mechanism for an inhaler comprising,
a storage chamber of medicament arranged above a moving trailing bottom configured to support and hold the medicament within the storage chamber and to move axially as the medicament is removed from the storage chamber;
a transparent wall;
a display comprising a strip tape that is engaged with a portion of the trailing bottom and moves a distance proportional to the movement of the trailing bottom such that the display is visible through the transparent wall, where the engagement of the strip tape with the portion of the trailing bottom causes the strip tape to be deflected by 180° and occurs at a deflection area behind and visible through the transparent wall.

2. The dosing mechanism of claim 1 where the deflection area is an outer deflection area located on an outer surface, where the portion of the trailing bottom has an inner surface having an inner deflection area, and where the inner surface is beveled to a greater degree than the outer surface.

3. A dosing device for inhaling a powdery substance, the dosing device comprising, a storage chamber having a longitudinal axis, wherein the powdery substance is arranged in the storage chamber, wherein the storage chamber is arranged above a trailing bottom, where the trailing bottom is configured
to allow the powdery substance to be retrieved from the storage chamber and brought into an emptying readiness position, and
to move parallel to the longitudinal axis as the powdery substance is retrieved from the storage chamber;
a transparent device wall; and
a display associated with the actual filling level, where the display comprises a strip tape which is engaged with a portion of the trailing bottom and which is deflected by 180° in a deflection area, wherein the deflection area of the strip tape is visible through the transparent device wall.

* * * * *